United States Patent
Almeida et al.

(10) Patent No.: US 9,744,477 B2
(45) Date of Patent: Aug. 29, 2017

(54) PURGE METHOD FOR LOW PRESSURE GRADIENT FORMATION LIQUID CHROMATOGRAPHY

(71) Applicant: Waters Technologies Corporation, Milford, MA (US)

(72) Inventors: Neal B. Almeida, Cumberland, RI (US); Christopher Seith, Franklin, MA (US); Michael R. Jackson, Woonsocket, RI (US); John Angelosanto, North Attleboro, MA (US); Joseph A. Jarrell, Newton Highlands, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 151 days.

(21) Appl. No.: 14/696,572

(22) Filed: Apr. 27, 2015

(65) Prior Publication Data

US 2015/0336026 A1  Nov. 26, 2015

Related U.S. Application Data

(60) Provisional application No. 62/001,896, filed on May 22, 2014.

(51) Int. Cl.
*F16K 11/22* (2006.01)
*B01D 15/18* (2006.01)
*G01N 30/26* (2006.01)
*G01N 30/34* (2006.01)

(52) U.S. Cl.
CPC .............. *B01D 15/18* (2013.01); *G01N 30/26* (2013.01); *G01N 30/34* (2013.01); *Y10T 137/0424* (2015.04); *Y10T 137/4259* (2015.04)

(58) Field of Classification Search
CPC ................. G01N 30/34; G01N 30/347; G01N 2030/326; G01N 2030/347; B01D 15/166; B01D 15/18
USPC ..... 137/605, 606; 210/101, 143, 198.2, 656; 422/70
See application file for complete search history.

(56) References Cited

U.S. PATENT DOCUMENTS 4,116,046 A  * 9/1978 Stein ................. G01N 30/24
                                              210/198.2
5,234,587 A  * 8/1993 Allington ............... G01N 30/34
                                              210/101

(Continued)

OTHER PUBLICATIONS

Agilent Technologies, "Agilent 1260 Refractive Index Detector User Manual", Rev. B, Agilent.com, 2010, 2012; 174 pages.

*Primary Examiner* — Reinaldo Sanchez-Medina
(74) *Attorney, Agent, or Firm* — Schmeiser, Olsen & Watts LLP

(57) ABSTRACT

Described is a method for purging a fluid channel is a low pressure gradient formation liquid flow system. Control of the fluid channels for multiple solvents allows for one or more static volumes of solvents not intended for use in an isocratic flow to be purged from their fluid channels to avoid contamination of the isocratic solvent. Advantageously, the method avoids the need to modify equipment or to reconfigure a pumping system so that the inlet is directly coupled to a single solvent source. Thus there is no need to bypass existing valves and liquid coupling components where solvents are combined during conventional gradient operation.

5 Claims, 20 Drawing Sheets

(56) References Cited

U.S. PATENT DOCUMENTS

| | | | |
|---|---|---|---|
| 2002/0134143 A1* | 9/2002 | Allington | B01D 15/12 |
| | | | 73/61.58 |
| 2006/0201885 A1* | 9/2006 | Davison | B01D 15/16 |
| | | | 210/656 |
| 2007/0144977 A1* | 6/2007 | Kitagawa | G01N 30/34 |
| | | | 210/787 |
| 2013/0008535 A1* | 1/2013 | Aso | G01N 30/34 |
| | | | 137/565.01 |
| 2014/0227134 A1* | 8/2014 | Joost | A61M 1/1698 |
| | | | 422/48 |

* cited by examiner

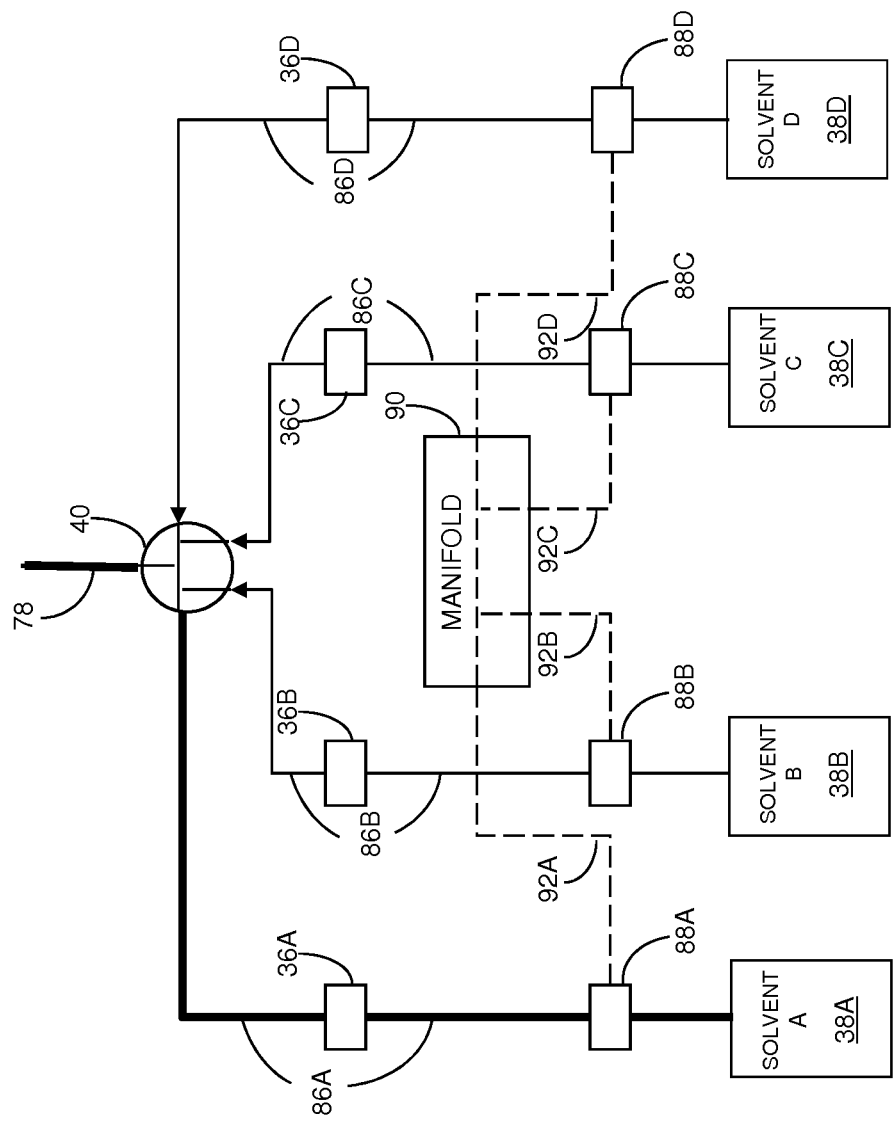

PURGE METHOD FOR LOW PRESSURE GRADIENT FORMATION LIQUID CHROMATOGRAPHY

RELATED APPLICATION

This application claims the benefit of the earlier filing date of U.S. Provisional Patent Application Ser. No. 62/001,896, filed May 22, 2014 and titled "Purge Method for Low Pressure Gradient Formation Liquid Chromatography," the entirety of which is incorporated herein by reference.

FIELD OF THE INVENTION

The invention relates generally to low pressure gradient formation flow systems such as those used in liquid chromatography. More particularly, the invention relates to a method for purging fluid channels having static fluid volumes that are not intended for use in an isocratic flow.

BACKGROUND

In a low pressure gradient liquid chromatography system, two or more liquids are combined in proportions according to a defined gradient composition. The contribution of the liquids to the flow is controlled using a set of valves with each liquid being controlled by a single one of the valves. Each liquid travels from the respective valve through a fluid channel to a cross connection in the system where the liquids are combined into a single flow having the specified gradient composition. The static volume in the fluid channel between a valve and the cross connection can be a source of contamination when the liquid in that fluid channel is not intended for use.

The liquid chromatography system may be operated in isocratic mode by maintaining a single valve in an open state while keeping the other valves closed. If the system remains idle for an extended period of time, liquids disposed in the unused fluid channels between each valve and the cross connection can migrate past the cross connection and into a downstream fluid channel that contains a different liquid. Subsequent operation of the system with the contaminated mobile phase can result in noise and drift in the isocratic chromatographs, and may reduce the accuracy of measurement data.

SUMMARY

In one aspect, a method for purging a fluid channel in a low pressure gradient formation liquid flow system having a cross connection, a first valve in communication with the cross connection through a first fluid channel, a second valve in communication with the cross connection through a second fluid channel, and a pump system in communication with the cross connection through a third fluid channel, wherein the first fluid channel having a volume containing a first liquid and the second fluid channel having a volume containing a second liquid, includes drawing the first liquid from the first valve through the first fluid channel, the cross connection, the third fluid channel and the pump system. The method further includes closing the first valve to prevent flow between the cross connection and the first valve and opening the second valve to permit flow between the cross connection and the second valve. The first liquid is supplied from the pump system through the third fluid channel, the cross connection, and the second fluid channel to at least the second valve to thereby replace the volume of the second liquid in the second fluid channel with the first liquid. The second valve is closed to thereby prevent flow between the second valve and the cross connection.

In another aspect, a low pressure gradient formation liquid flow system includes a first valve, a second valve, a cross connection, a pump system and a processor. The cross connection is in communication with the first and second valves through a first fluid channel and a second fluid channel, respectively. The pump system is in communication with the cross connection through a third fluid channel. The processor is in communication with the first and second valves and the pump system. The processor is configured to control the first and second valves to be in an open state or a close state and is further configured to control the pump system to draw liquid from the cross connection or to supply liquid to the cross connection. The processor is configured to operate in a first processor state in which the first valve and the second valve are maintained in an open state and a closed state, respectively, and the pump system is operated to draw a first liquid from the first valve through the first fluid channel, the cross connection, the third fluid channel and the pump system. The processor is configured to operate in a second processor state in which the first valve and the second valve are maintained in a closed state and an open state, respectively, and the pump system supplies the first liquid from the pump system through the third fluid channel and the cross connection to at least the second valve to thereby replace a second liquid in the second fluid channel with the first liquid. The processor is configured to operate in a third processor state in which the second valve is maintained in a closed state.

In yet another aspect, a method for purging a fluid channel in a low pressure gradient formation liquid flow system having a cross connection, a first two-position divert valve in communication with the cross connection through a first fluid channel, a second two-position divert valve in communication with the cross connection through a second fluid channel and in communication with the first two-position divert valve through a third fluid channel, a first valve disposed inline in the first fluid channel and a second valve disposed inline in the second fluid channel, wherein the first and second two-position divert valves are configured to pass a received liquid to the first and second fluid channels, respectively, when each is in a first state and to conduct a liquid between the first and second two-position divert valves through the third fluid channel when each is in a second state, includes (a) drawing a first liquid from the first two-position divert valve through the first fluid channel and the cross connection when the first two-position divert valve is in the first state and the first valve is in an open state. The method further includes (b) drawing the first liquid from the first two-position divert valve through the third fluid channel, the second two-position divert valve and the second fluid channel to at least the cross connection when the first and second two-position divert valves are in the second state and the second valve is in an open state, wherein a second liquid present in the second fluid channel prior to step (b) is displaced from the second fluid channel though the cross connection by the first fluid.

In still another aspect, a low pressure gradient formation liquid flow system includes a cross connection, a first two-position divert valve in communication with the cross connection through a first fluid channel, and a second two-position divert valve in communication with the cross connection through a second fluid channel and in communication with the first two-position divert valve through a third fluid channel. The first and second two-position divert valves are configured to pass a received liquid to the first and second fluid channels, respectively, when each is in a first state and to conduct a liquid between the first and second two-position divert valves through the third fluid channel when each is in a second state. The low pressure gradient formation liquid flow system further includes a first valve disposed inline in the first fluid channel, a second valve disposed inline in the second fluid channel, and a pump system in communication with the cross connection through a fourth fluid channel. The low pressure gradient formation liquid flow system also includes a processor in communication with the first and second two-position divert valves, the first and second valves, and the pump system. The processor is configured to control the first and second valves to be in an open state or a closed state, is configured to control the first and second two-position divert valves to be in the first state or the second state, and is configured to control the pump system to draw liquid from the cross connection through the fourth fluid channel. The processor is further configured to operate in a first processor state in which the first two-position divert valve is in the first state, the first valve is in the open state and the pump system draws a first liquid through the first two-position divert valve, the first fluid channel and the cross connection. The processor is also configured to operate in a second processor state in which the first and second two-position divert valves are in the second state, the first and second valves are in the closed and open states, respectively, and the pump system draws the first fluid from the first two-position divert valve through the third fluid channel, the second two-position divert valve, and the second fluid channel to at least the cross connection to thereby replace a second liquid previously contained in the second fluid channel with the first liquid.

In still another aspect, a method for purging a fluid channel in a low pressure gradient formation liquid flow system having a cross connection, a first valve in communication with the cross connection through a first fluid channel, a second valve in communication with the cross connection through a second fluid channel, and a pump system in communication with the cross connection through a third fluid channel, the first fluid channel having a volume containing a first liquid and the second fluid channel having a volume containing a second liquid, includes controlling the second valve to prevent the flow of liquid in the second fluid channel. The first liquid is drawn through the first fluid channel to the pump system so that the first liquid occupies the first channel and the third channel. The first valve is controlled to prevent the flow of liquid in the first fluid channel and the second valve is controlled to enable the flow of liquid in the second channel. The pump system is controlled to push the first liquid in the third channel into the second channel to substantially replace the second liquid in the second channel with the first liquid.

In still another aspect, a method for purging a fluid channel in a low pressure gradient formation liquid flow system having a cross connection, a first valve in communication with the cross connection through a first fluid channel, a second valve in communication with the cross connection through a second fluid channel, and a pump system in communication with the cross connection through a third fluid channel, the first fluid channel having a volume containing a first liquid and the second fluid channel having a volume containing a second liquid, includes controlling the second valve to prevent the flow of liquid in the second fluid channel. The first liquid is drawn through the first fluid channel to the pump system so that the first liquid occupies the first channel and at least a portion of the third channel. The second valve is controlled to enable the flow of liquid in the second fluid and the first valve is controlled to prevent the flow of the first liquid in the first fluid channel toward the cross connection. A flow of the first liquid is drawn from the first channel through the second channel and the cross connection to thereby displace the second liquid from the second channel into the third channel. The first and second valves are controlled to enable the flow of liquid in one of the first and second channels and to prevent the flow of liquid in the other of the first and second channels. A flow of the first liquid is drawn from one of the first and second channels through the cross connection and into the third channel to thereby displace the second liquid from the third channel.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

FIG. 10A through FIG. 10E show the block diagram of FIG. 9 and illustrate the flow of solvents according to the method of FIG. 11.

DETAILED DESCRIPTION

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

In brief overview, the invention relates to a method for purging a fluid channel is a low pressure gradient formation liquid flow system. Control of the fluid channels for multiple solvents allows for one or more static volumes of solvents not intended for use in an isocratic flow to be purged from their fluid channels to avoid contamination of the isocratic solvent. Advantageously, the method avoids the need to modify equipment or to reconfigure a pumping system so that the inlet is directly coupled to a single solvent source. Thus there is no need to bypass valves (e.g., a gradient proportioning valve) and any downstream cross connection where solvents are combined under conventional gradient operation.

The present teaching will now be described in more detail with reference to embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

Figure 1:
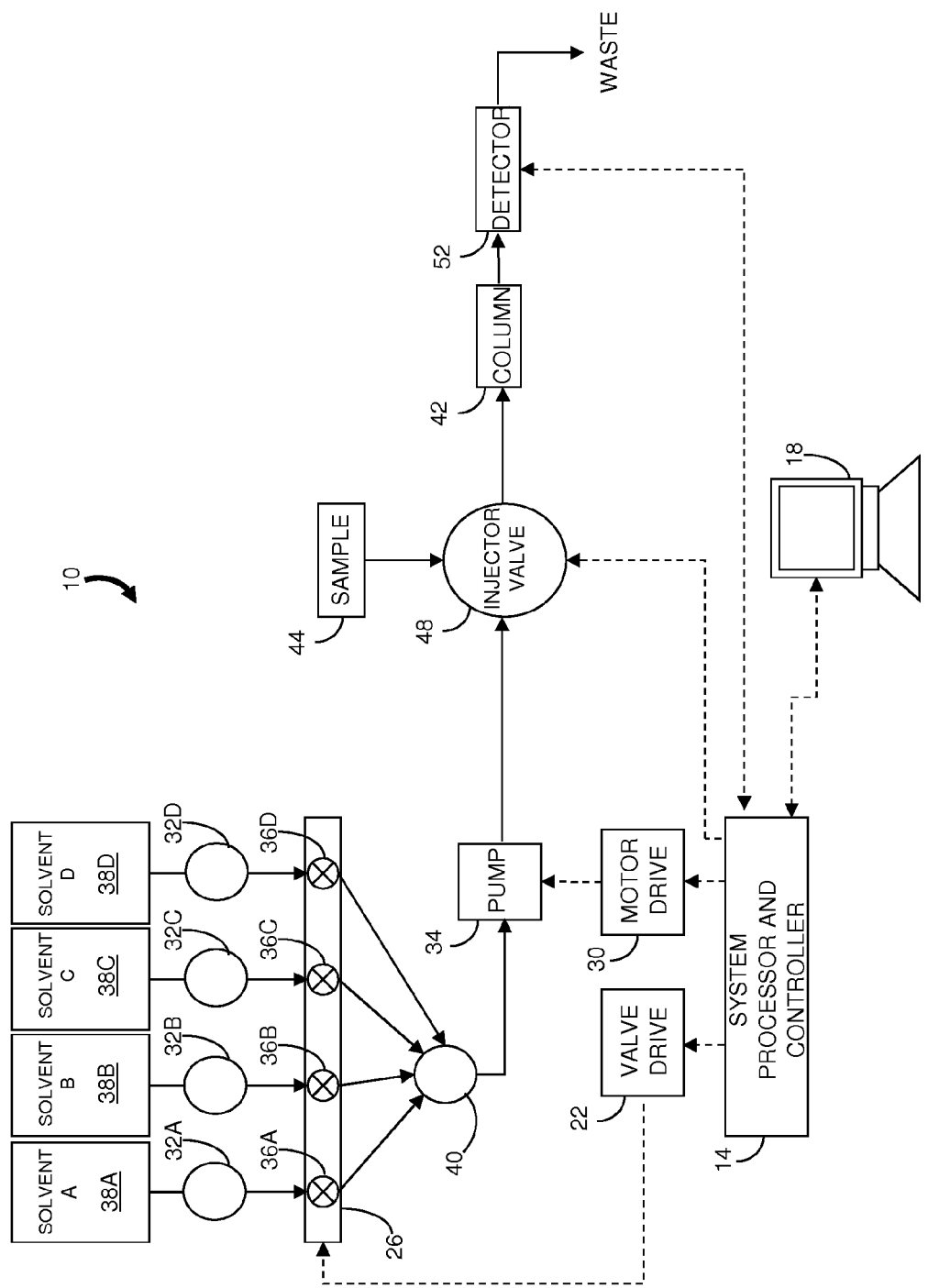
FIG. 1 is a block diagram of a liquid chromatography system that can be used to practice embodiments of a method for purging a fluid channel in a low pressure gradient formation liquid flow system.

FIG. 1 is a block diagram of a liquid chromatography system 10 that can be used to practice the method of the invention. The system 10 includes a system processor 14 (e.g., microprocessor and controller) in communication with a user interface device 18 for receiving input parameters and displaying system information to an operator. The system processor 14 communicates with a valve drive module 22 for controlling operation a gradient proportioning valve (GPV) 26 and communicates with a motor drive module 30 for controlling operation of one or more stepper motors in a pump system 34. The pump system 34 can include pump heads that may be configured in a variety of ways. For example, the pump system 34 can include a primary pump head in serial communication with an accumulator pump head.

The gradient proportioning valve 26 includes a plurality of valves 36A, 36B, 36C and 36D which in turn are coupled by tubing to solvent reservoirs 38A, 38B, 38C and 38D, respectively, that hold the solvents to be combined as a mobile phase. Each valve 36 generally operates in either an open state in which a liquid is allowed to flow or in a closed state in which the flow of liquid is prevented. Degassers 32A, 32B, 32C and 32D between the solvent reservoirs 38 and the GPV 26 operate to remove dissolved gas in the solvents drawn from the reservoirs 38. The degassers 32 can be independent degassers, as illustrated, or may be integrated into a single degas ser unit where all four solvents pass through a common vacuum region of the degasser.

Each valve 36 is coupled to one of four inlet ports of a cross connection 40. The single outlet port of the cross connection is coupled to the inlet port of the pump system 34. The outlet port of the pump system 34 provides the mobile phase comprising the mixture of solvents to a fluid channel leading to a chromatographic column 42. The mobile phase is generally at a substantially higher pressure than the solvents upstream from the GPV 26. A sample from a sample reservoir, or sample container, 44 is injected into the mobile phase upstream from the chromatographic column 42 using an injector valve 48. The chromatographic column 42 is coupled to a detector 52 which provides a signal to the system processor 14 that is responsive to various components detected in the eluent.

During operation of the liquid chromatography system 10 using a gradient mobile phase, the valves 36 are opened sequentially so that the pump system 34 draws liquid from each of the reservoirs 38 that contribute a solvent to the mobile phase. The proportions of solvents present in the liquid mixture delivered by the pump system 34 depend on the relative actuation time of each of the valves 36. Actuation times generally change throughout the gradient mobile phase according to changes in the gradient composition ratios over the duration of the gradient process.

High sensitivity detectors have been developed that can more accurately determine and quantify the presence of various analytes in the eluent from the chromatography column 42. For example, the liquid chromatography system 10 can include a refractive index detector which senses changes in the refractive index of the eluent over time according to the retention times of various analytes present in the injected sample. A change in the composition of the mobile phase typically changes the refractive index. Consequently, refractive index detectors are generally only used for operation in an isocratic mode. Moreover, a change in the purity of the mobile phase or a change due to the presence of dissolved air in the mobile phase can result in noise in the acquired data. The degassers 32 operate to remove any dissolved gas in the solvents; however, various means of mobile phase contamination exist which can add noise to the liquid chromatography measurement data.

Figure 2:
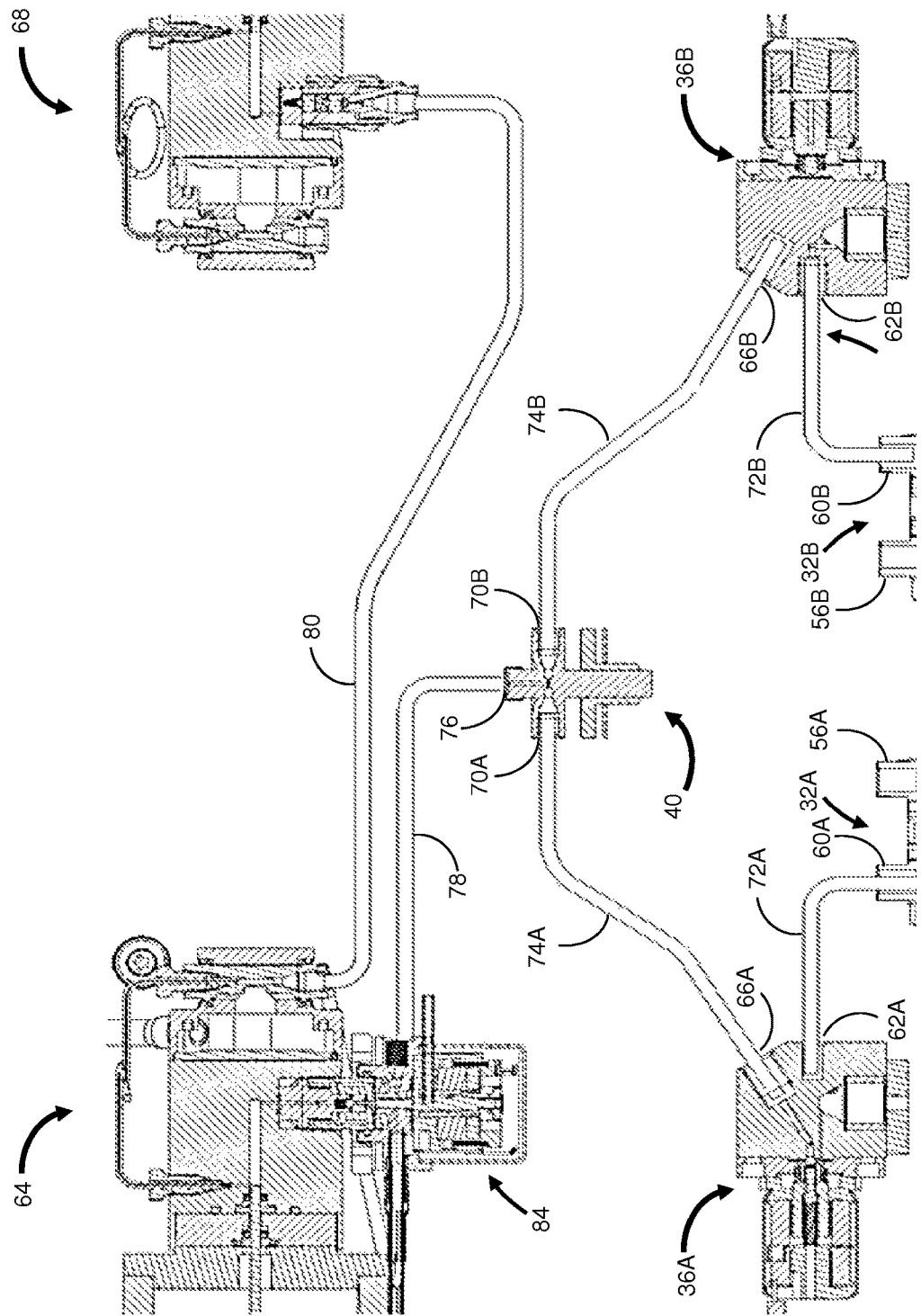
FIG. 2 is a block diagram of a portion of the solvent management components for the liquid chromatography system of FIG. 1.

FIG. 2 shows a detailed view of a portion of the solvent management components for the liquid chromatography system 10 of FIG. 1. In particular, the inlets 56A and 56B, and outlets 60A and 60B of two of the degassers 32A and 32B, the corresponding valves 36A and 36B of the GPV 26, the cross connection 40 and a portion of the pump system are shown. The pump system includes a primary pump head 64 and accumulator pump head 68, only a portion of each pump head 64 and 68 is shown in the figure.

The outlets 60A and 60B of the degassers 32A and 32B, respectively, are coupled to the inlets 62A and 62B of valves 36A and 36B, respectively, through fluid channels 72A and 72B, respectively. The outlets 66A and 66B of valves 36A and 36B are coupled to the inlets 70A and 70B, respectively, of cross connection 40 through fluid channels 74A and 74B, respectively. The single outlet 76 of the cross connection 40 is coupled to the primary pump head 64 through a fluid channel 78 and the primary pump head 64 is coupled through a fluid channel 80 to the accumulator pump head 68. Not shown are the fluidic channels that couple the inlets 56A and 56B of the degassers 32A and 32B to their respective solvent reservoirs 38A and 38B.

Although not shown in FIG. 2 to maintain clarity, it should be understood that the other two degassers 32C and 32D are similarly coupled through fluid channels to their valves 36C and 36D which in turn are coupled through fluid channels to other inlets of the cross connection 40. The liquid chromatography system thus has the capability to operate in isocratic or gradient modes with a mobile phase that is a selection of a single one of the solvents or a mixture of two or more of the four solvents. For example, the system is capable of operating in a binary gradient mode or a quaternary gradient mode.

In the following description of operation of the liquid chromatography system, reference is made to figures which depict fluid channels only for solvents A and B; however, it will be understood that the description can be expanded such that operation can similarly be performed using, in addition, solvent C and/or solvent D.

Figure 3:
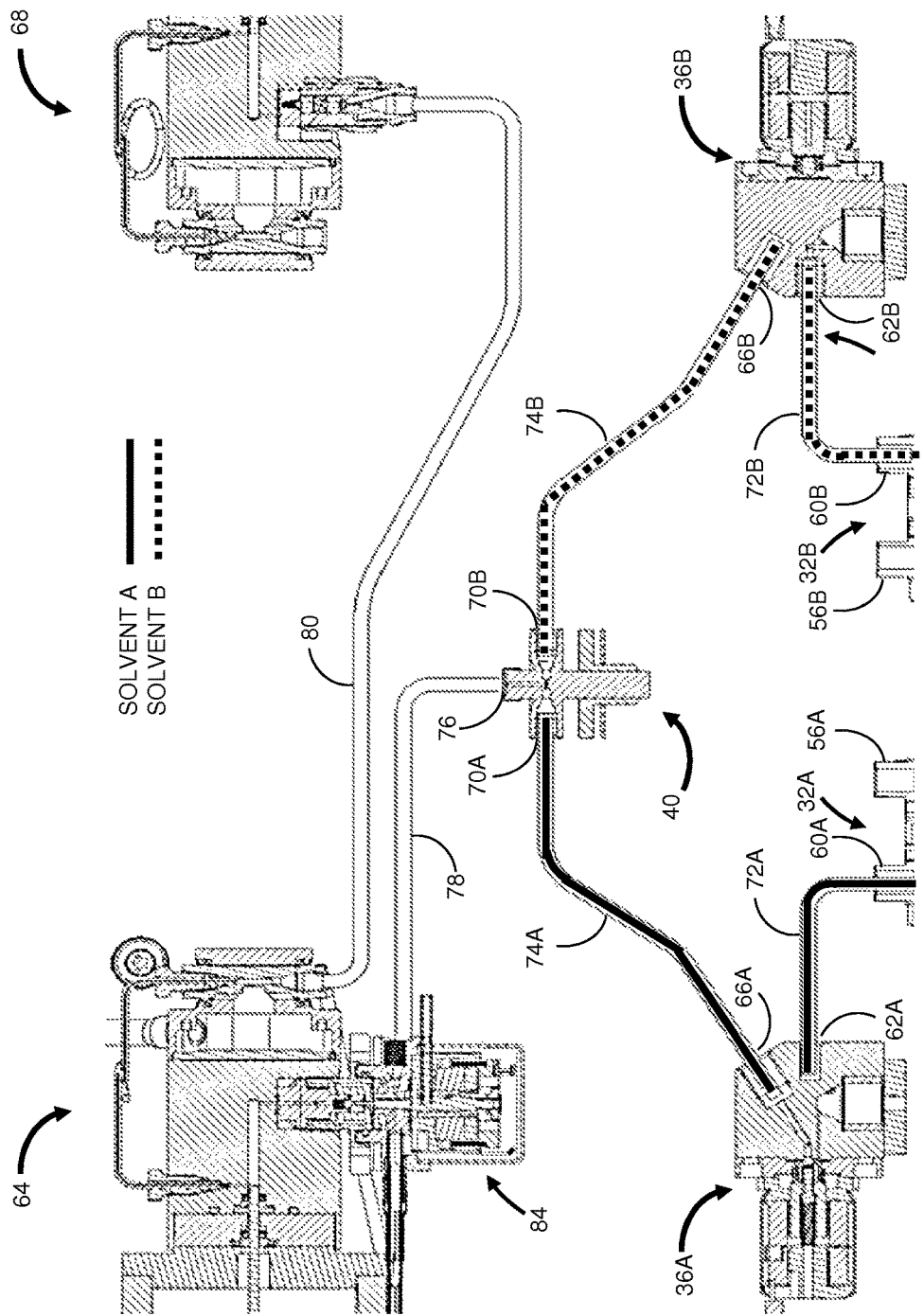
FIGS. 3, 4 and 5 show the solvent management components of FIG. 2 in various configurations for operation with two solvents A and B.

FIG. 3 shows the liquid chromatography system in a configuration primed for operation with solvents A and B. Thus solvent A is fully occupies the solvent path defined by fluid channels 72A and 74A, and solvent B fully occupies the solvent path defined by fluid channels 72B and 74B.

Figure 4:
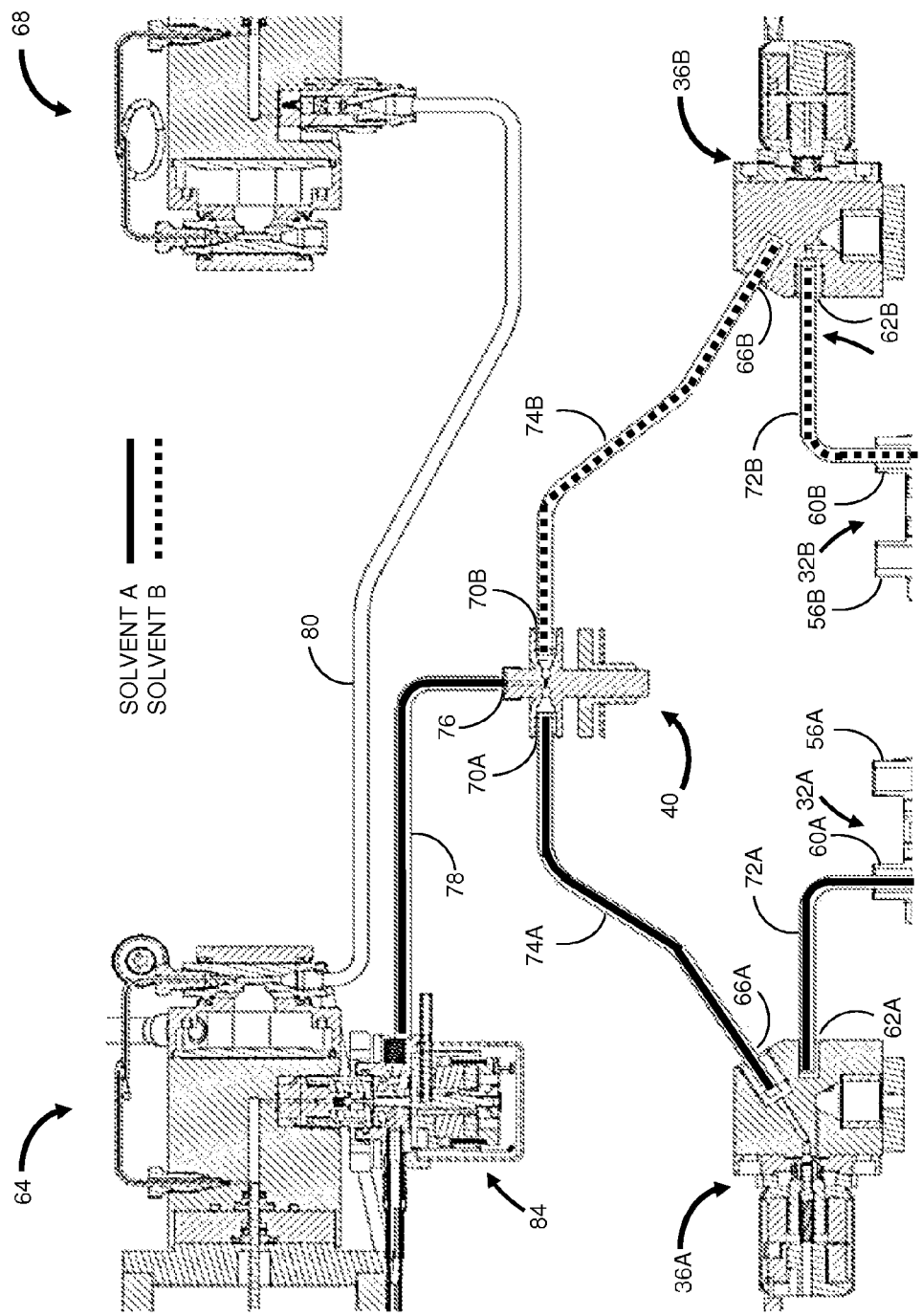
Figure 5:
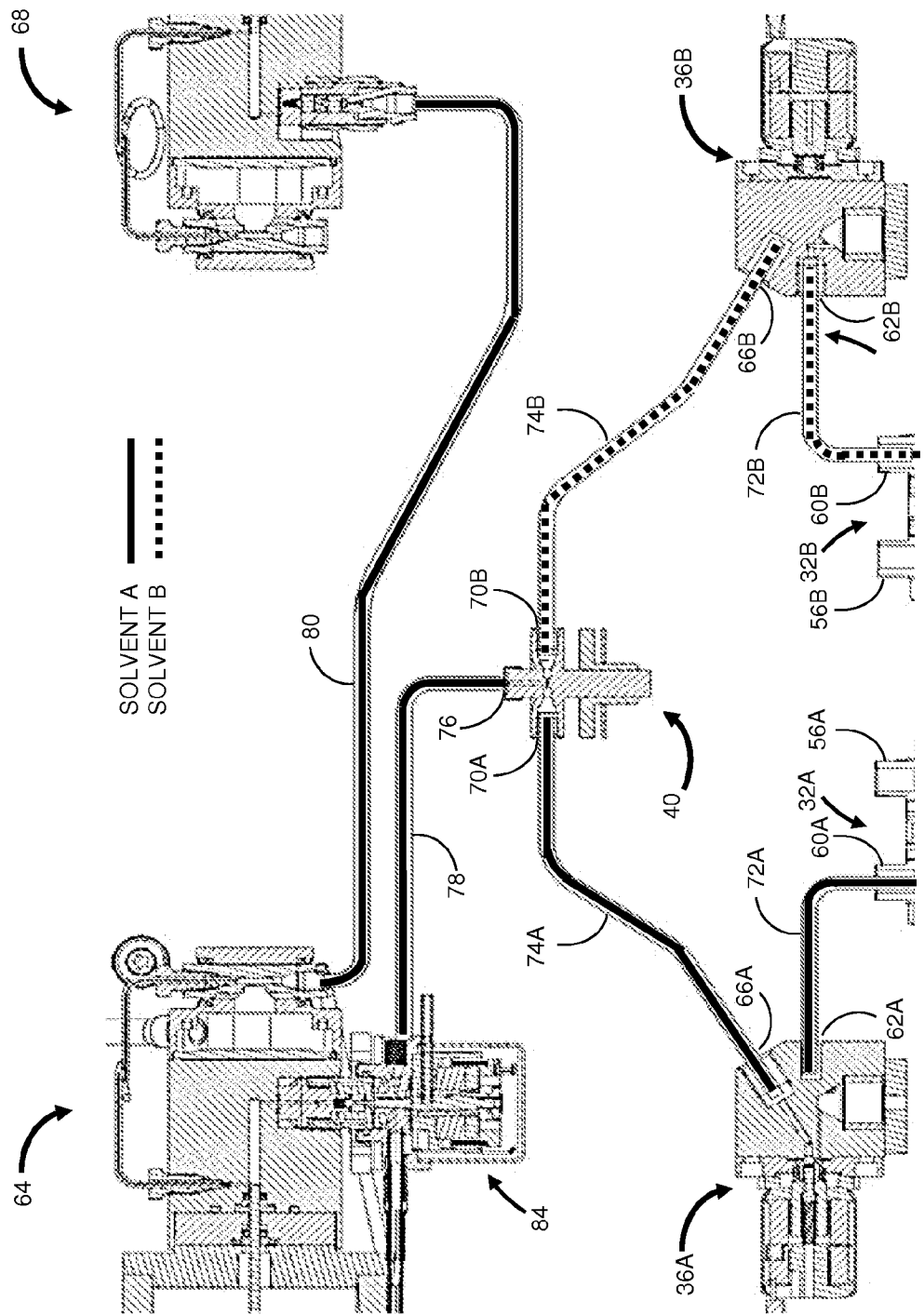

The system is subsequently intended for operation in isocratic mode such that the mobile phase includes only solvent A. Thus valve 36A is actuated and maintained in an open state so that solvent A is drawn from the cross connection 40 through fluid channel 78 to the primary pump head 64 as shown in FIG. 4. The other valves 36B, 36C and 36D are maintained in a closed state so that solvents B, C and D are not drawn past the cross connection 40. FIG. 5 shows the liquid chromatography system at a subsequent time when solvent A is drawn through the fluid channel 80 between the two pump heads 64 and 68 as appropriate for isocratic mode operation with a single solvent.

Figure 6A:
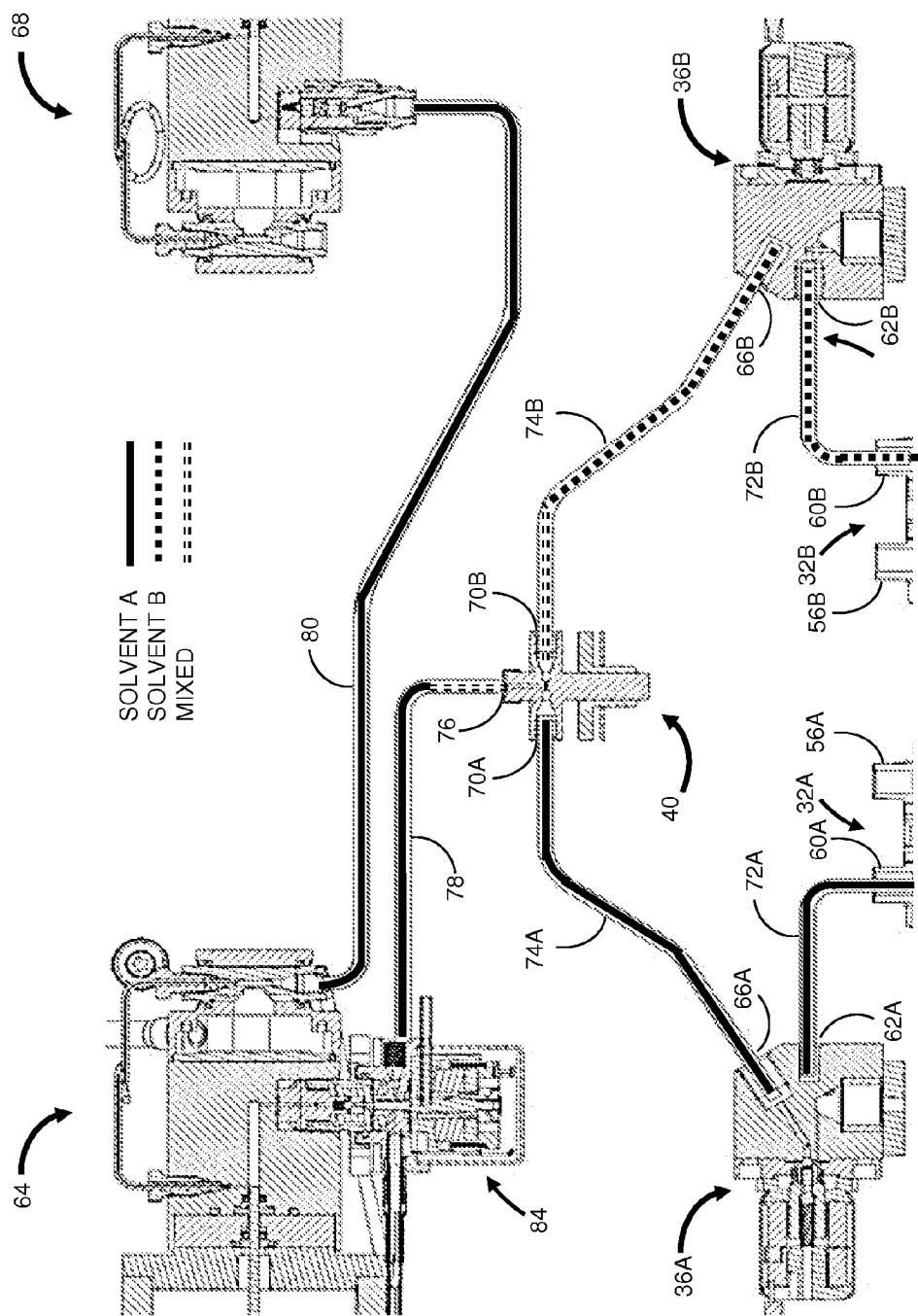
FIGS. 6A, 6B and 6C illustrate how a static volume of solvent B slowly migrates through a cross connection to mix with solvent A for the solvent management components shown in FIG. 2.

In an ideal configuration, the valves 36 would be co-located with the cross connection 40 so that there could be no fluidic communication between the solvents B, C and D at their respective cross connection inlets 70 with solvent A in the fluid channel 78 leading from the outlet 76 to the primary pump head 64. Such a configuration is generally not possible for physically distinct components. Over time, the static volume of solvent B slowly migrates from fluid channel 74B through the cross connection 40 and mixes into solvent A in fluid channel 78 as shown in FIG. 6A. Similarly, a small volume of solvent A slowly migrates from fluid channel 78 through the cross connection 40 and into fluid channel 74B to mix with solvent B. The degree of migration for a given time typically varies according to properties of the solvent, such as density, diffusion rate, compressibility and miscibility. It should be understood that solvent migration does not mean the full displacement of one solvent by another solvent, but instead that a mixture of solvents occupy the indicated migration volumes in the fluid channels.

Figure 6B:
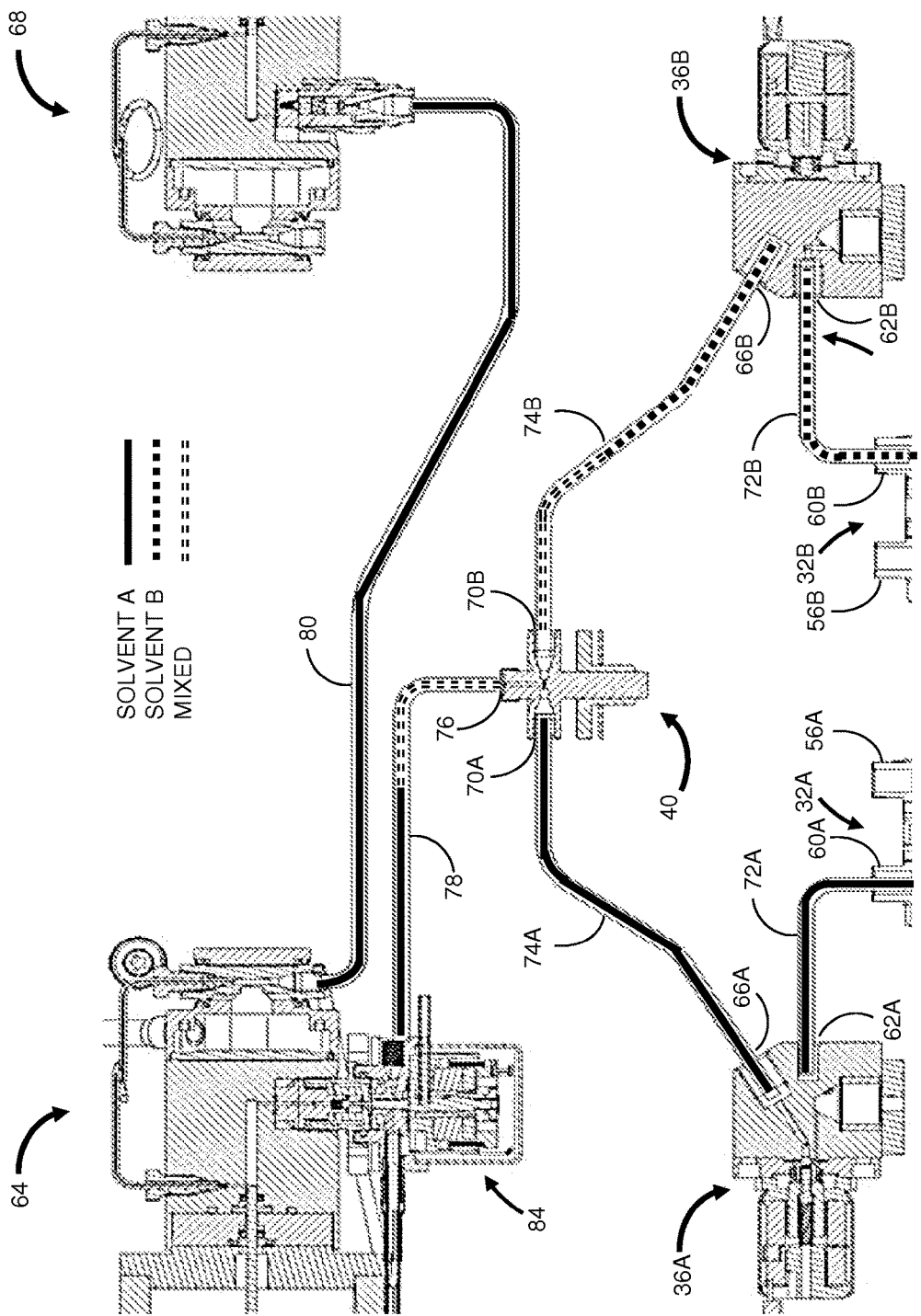
Figure 6C:
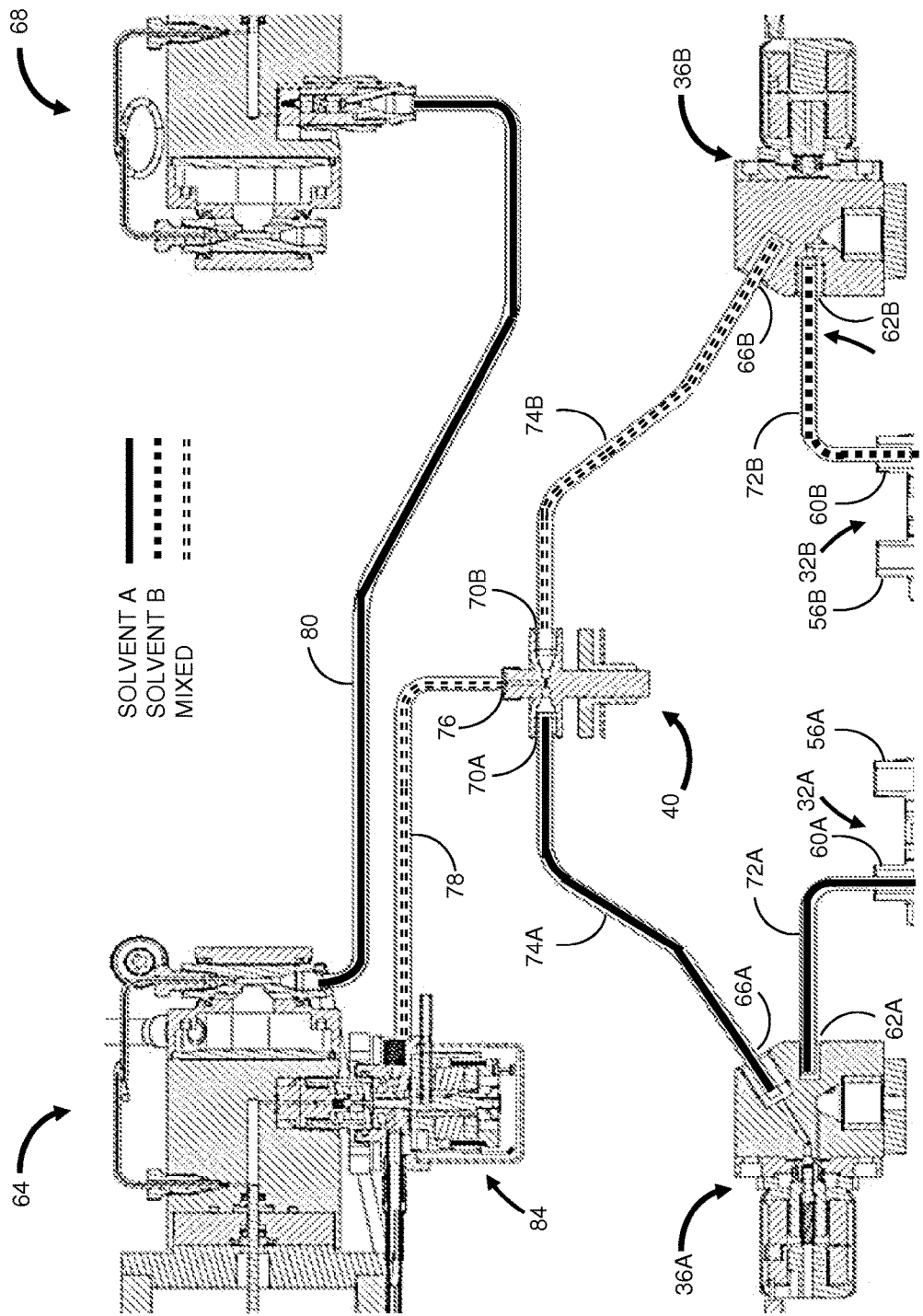

After the passage of additional time, the degree of migration can increase as shown in FIG. 6B. Eventually, the migration of solvents A and B continues until the entire volumes of fluid channels 74B and 78 may be affected as shown in FIG. 6C.

Further migration of solvent A is prevented at valve 36B which is closed; however, the presence of solvent B in fluid channel 78 contributes directly to the composition of the mobile phase and therefore adversely affects detection by the refractive index detector. It will be appreciated that contamination from additional solvents C and D, as described with respect to FIG. 1, can occur.

Prior to performing an isocratic separation using solvent A, an embodiment of a method for purging a fluid channel in a low pressure gradient formation liquid flow system can be used to ensure that the liquid in fluid channel 74B contains only solvent A. Thus any subsequent migration of solvent A from fluid channel 74B into the fluid channel 78 between the cross connection 40 and the primary pump head 64 will have no detrimental effect on the isocratic separation.

Figure 7:
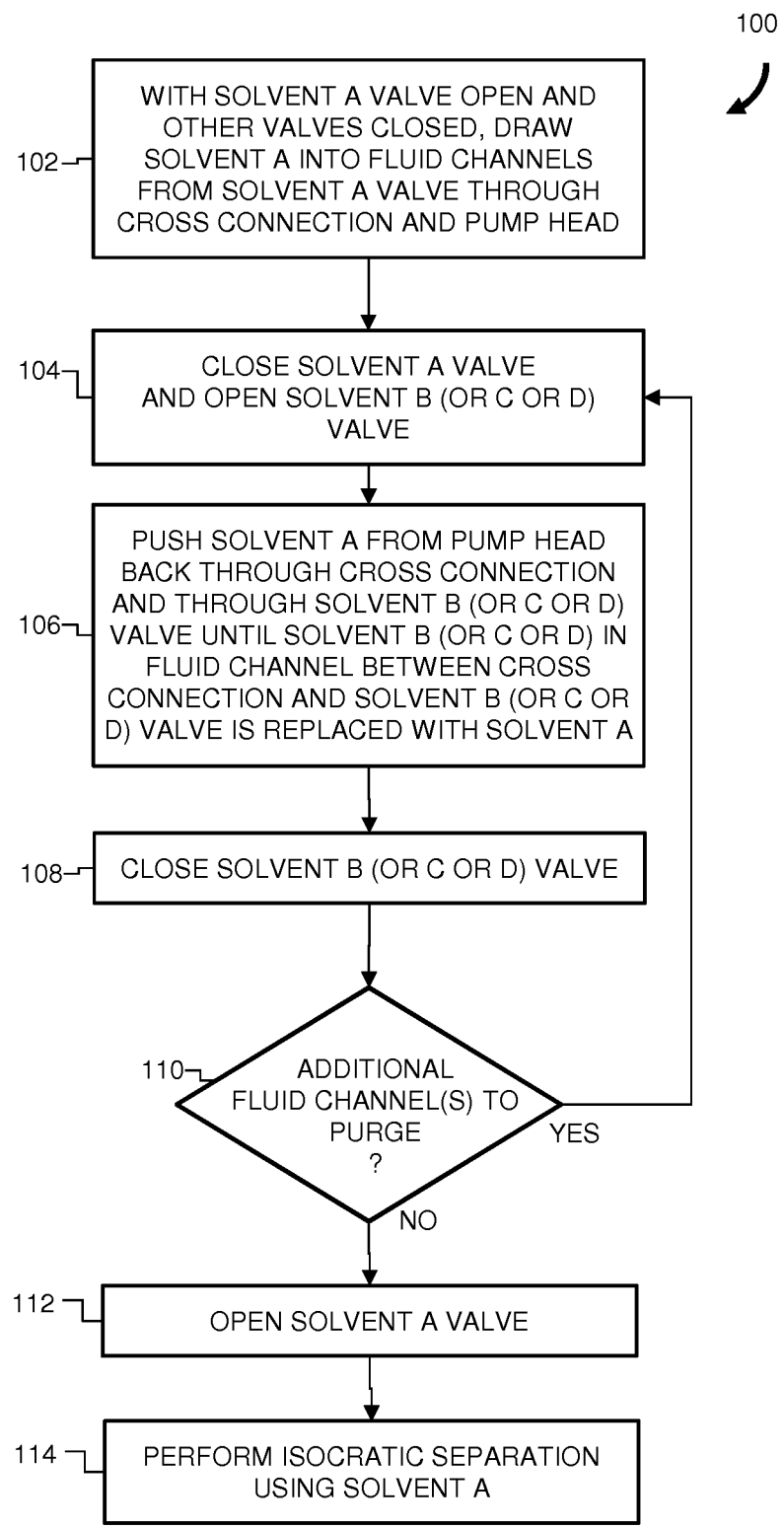
FIG. 7 is a flowchart of an embodiment of a method for reverse purging a fluid channel in a low pressure gradient formation liquid flow system.
Figure 8A:
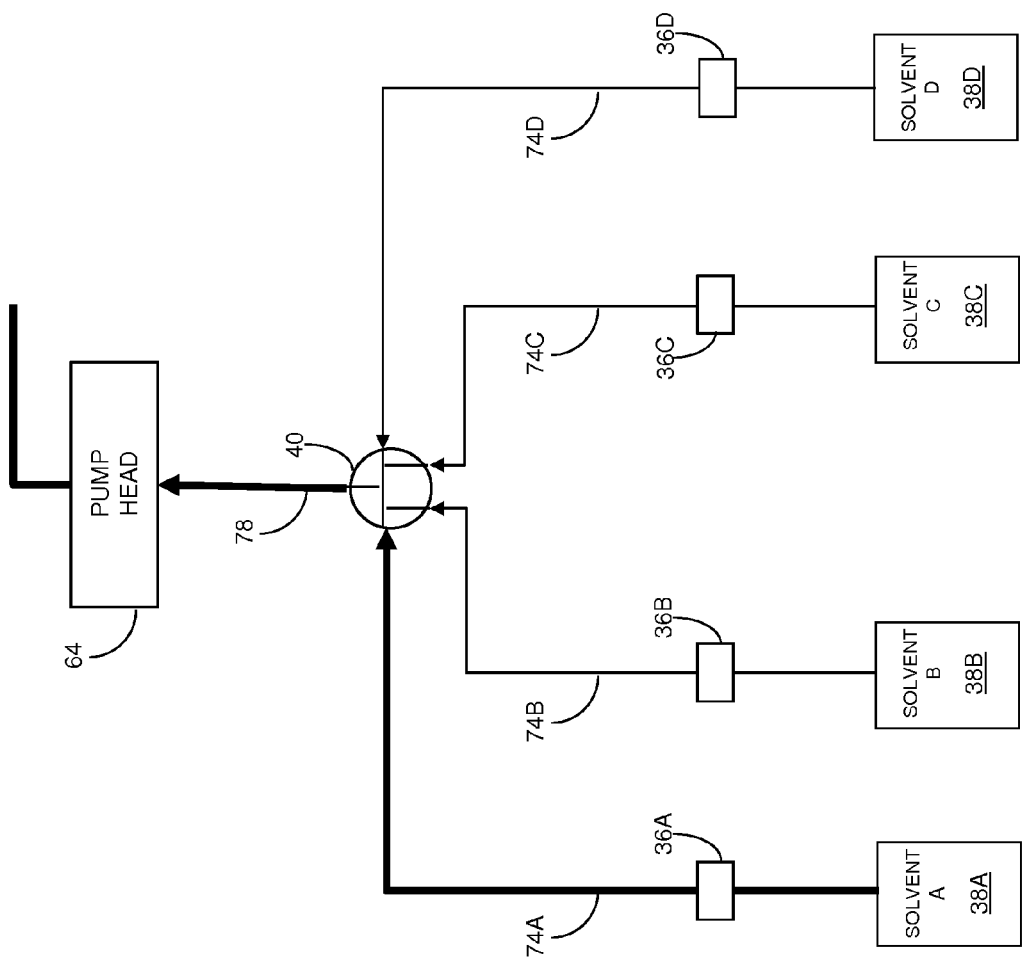
FIG. 8A through 8D show a block diagram of solvent management components and illustrate the flow of solvents according to the method of FIG. 7.

FIG. 7 shows a flowchart of an embodiment of the method 100. Initially, all the solvent valves 36 are closed except for the valve 36A for solvent A. Solvent A is drawn (102) into fluid channels 74A and 78, and through the primary pump head 64 as depicted by the bold lines in the block diagram of solvent management components in FIG. 8A. The valve 36A for solvent A is then closed and the valve 36B for solvent B is opened (104). A vent valve (not shown) that is downstream from a fluid channel leading from the outlet of the accumulator pump head 68 is closed and the inlet check valve 84 on the primary pump head 64 (see FIG. 2) is controlled for non-standard operation to allow liquid to flow in a reverse direction. Preferably, the inlet check valve 84 is an active check valve that is normally maintained in a closed state and is changed to an open state under assertion of a control signal, for example, during a pump intake stroke.

Figure 8B:
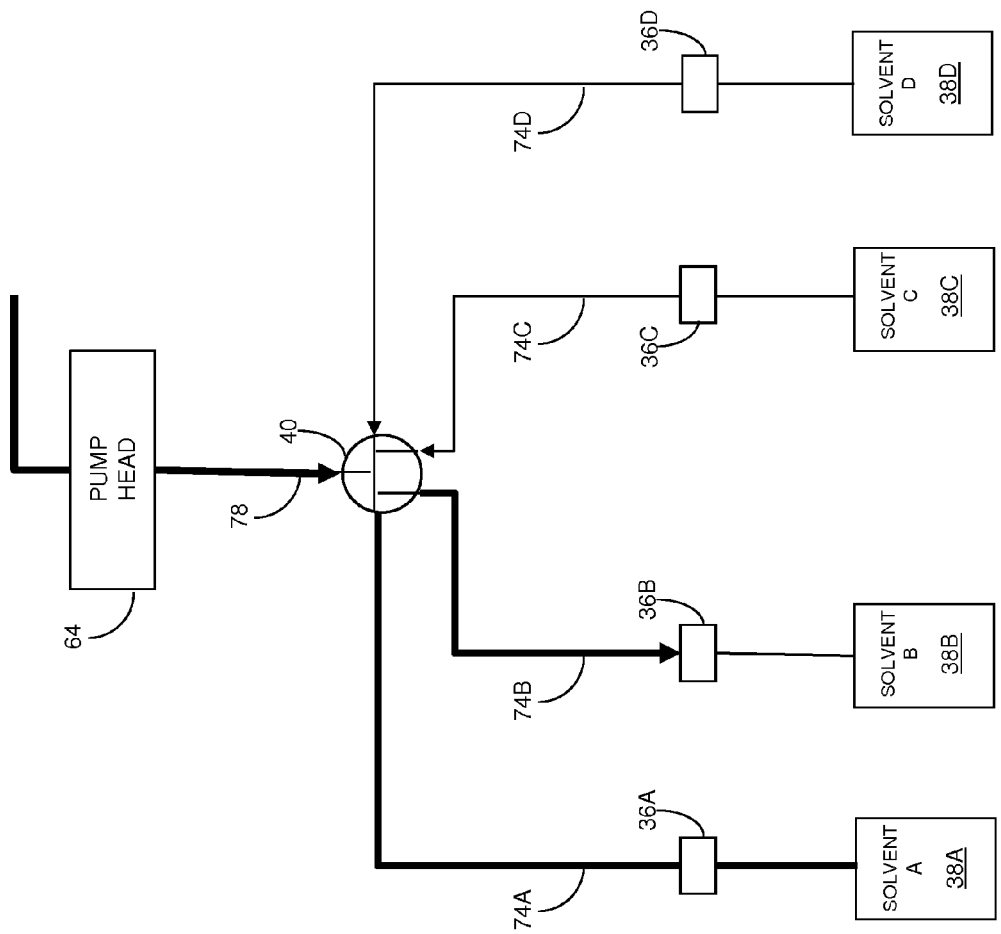

Subsequently, the primary pump head 64 is operated so that solvent A is pushed (106) in a reverse direction by maintaining the inlet check valve 84 in an open state. Consequently, solvent A flows backward, i.e., from the primary pump head 64 through the cross connection 40 and toward the solvent B valve 36B until the solvent B in the fluid channel 74B between the cross connection 40 and the valve 36B is replaced with solvent A. This process continues until all the solvent B previously in the fluid channel 74B is replaced by solvent A before closing (108) the solvent B valve 36B as shown in FIG. 8B. The volume of solvent A used to replace solvent B is accurately controlled so that a minimal amount of solvent A passes into the fluid channel 72B between the degasser 32B (see FIG. 2) and the valve 36B.

Figure 8C:
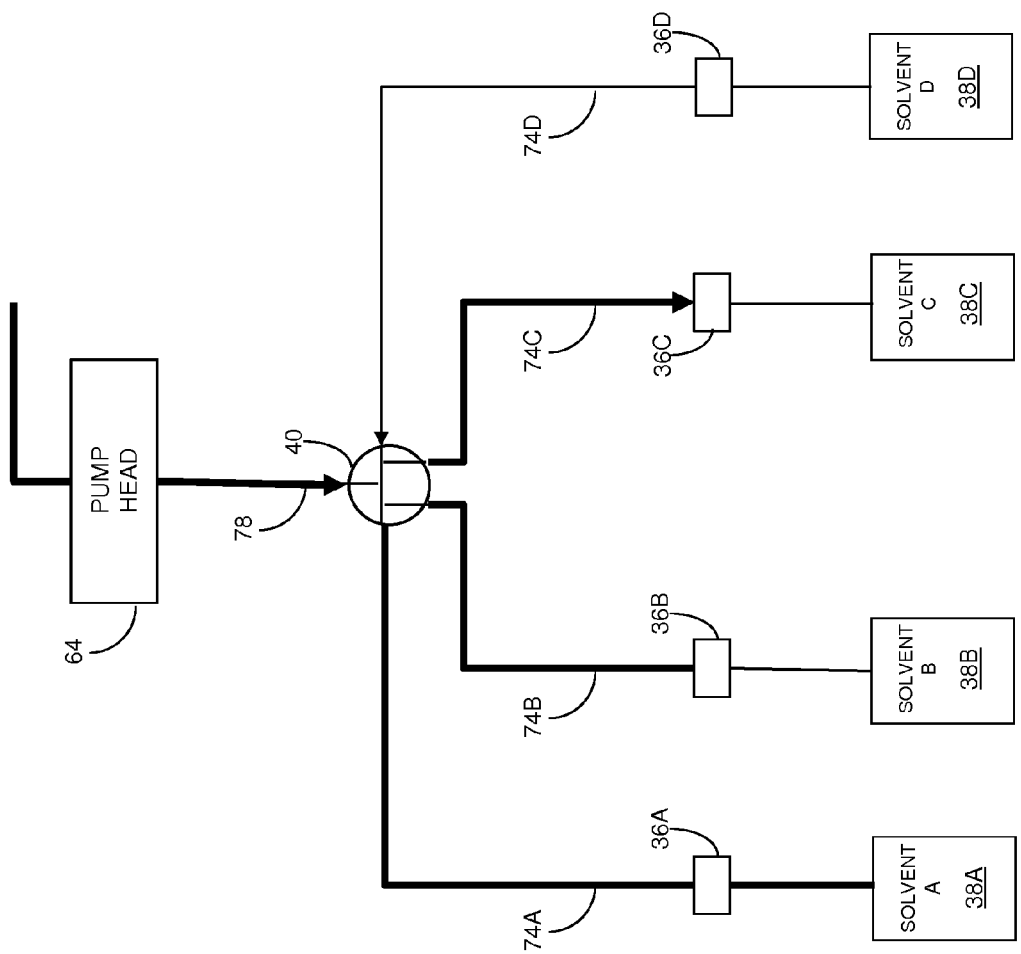
Figure 8D:
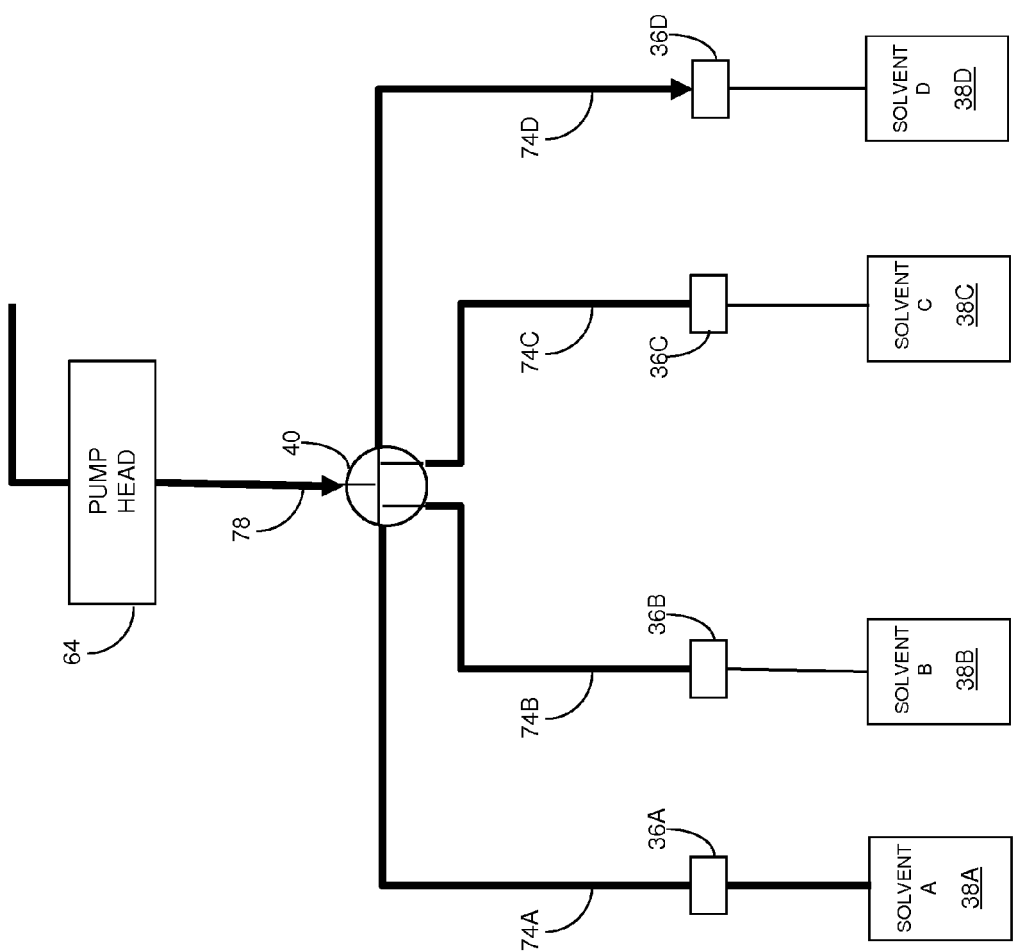

If one or more additional fluid channels remain to be purged (110), the method returns to repeat steps 104, 106 and 108 by operating the corresponding solvent valves 36 to allow replacement of the solvent in a fluid channel 74 with solvent A. Thus for a four channel solvent system, steps 104, 106 and 108 are performed a second time to achieve the result shown in FIG. 8C and a third time to achieve the result in shown FIG. 8D. Once all four fluid channels 74B contain solvent A, the solvent A valve 36A is opened (112) and an isocratic separation may be performed (114).

The embodiments described above are considered as back purge, or reverse purge, embodiments due to the reverse flow of solvent used to displace the pre-existing solvents in fluid channels 74B, 74C and 74D. Some embodiments are based on a flush forward process in which the solvent for isocratic operation flows in the normal forward direction to displace static volumes of the other solvents.

Figure 9:
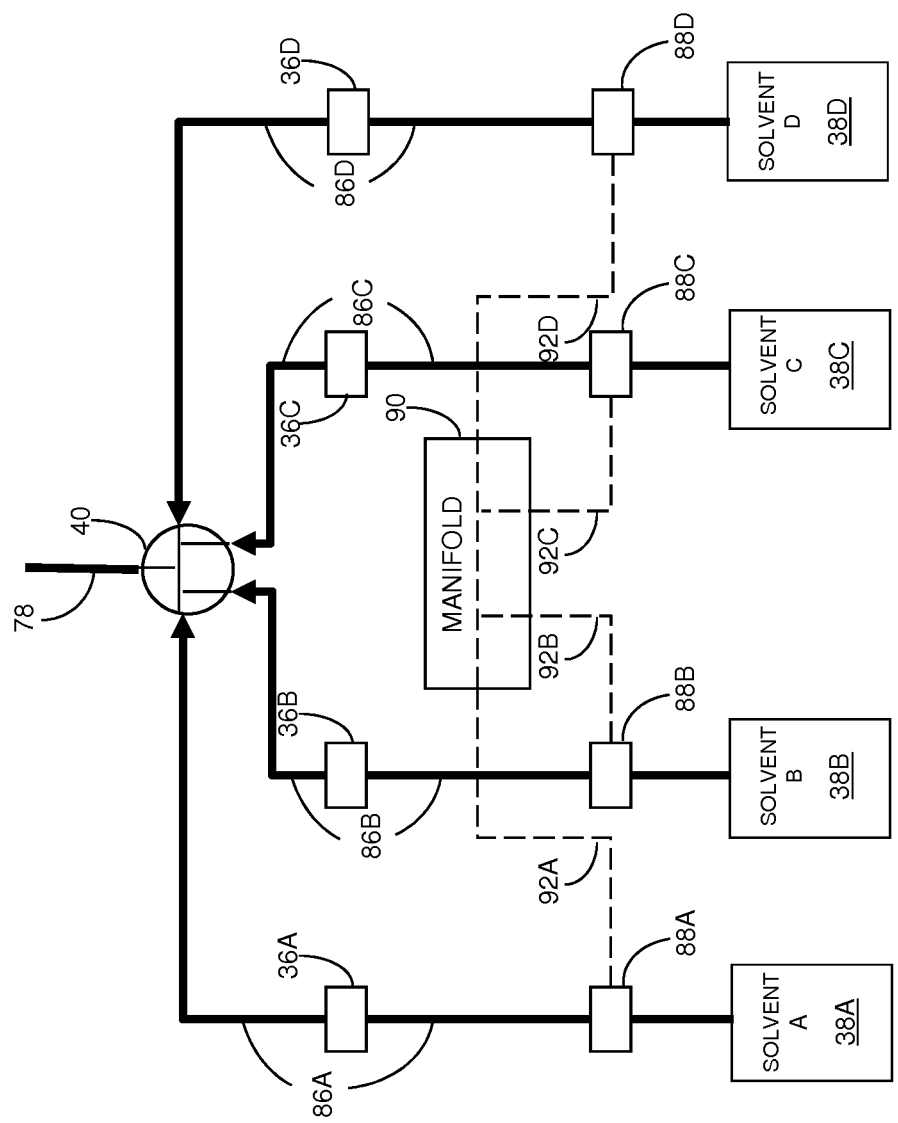
FIG. 9 is a block diagram of components of a solvent management system that can be used to practice an embodiment of a method for purging a fluid channel in a low pressure gradient formation liquid flow system.

FIG. 9 is a block diagram of components of a solvent management system that can be used to practice an embodiment of a method for purging a fluid channel in a low pressure gradient formation liquid flow system. Degassers disposed between the solvent reservoirs 38 and valves 36 (see degassers 32 in FIG. 1) are omitted for clarity. A cross connection 40 is in communication with a first port of each of four two-position divert valves 88 through a respective first fluid channel 86. A manifold 90 is in communication with a second port of the four two-position divert valves 88 through a respective second fluid channel 92. A valve 36 is disposed inline in each of the first fluid channels 86. A third port of each of the two-position divert valves 88 is in communication with a respective one of the solvent reservoirs 38.

The two-position divert valves 88 are configured to operate in a first (pass) state in which flow between the third and first ports is enabled and configured to operate in a second (divert) state in which flow between the third and second ports is enabled. The valves 36 operate in an open state in which liquid is permitted to flow within the first fluid channel 86 or in a closed state in which liquid is prevented from flowing in the first fluid channel 86. The valves 36 may be part of a GPV as described above. Depending on the states of the two-position divert valves 88 and valves 36, liquid can be made to flow from one two-position divert valve 88 through the manifold 90 to one or more other two-position divert valves 88.

Under normal operation for forming a gradient mobile phase in a liquid chromatography system, the two-position divert valves 88 are maintained in the first (pass) state to allow solvents from the reservoirs 38 to pass through to the valves 36. Two or more of the valves 36 can be modulated between their first and second states to pass volume contributions of the respective solvent to the cross connection 40 for generation of a gradient mobile phase.

In some circumstances, it may be desired to operate the liquid chromatography system in an isocratic mode. Thus the two-position divert valves 88 and valves 36 can be configured so that only one solvent is provided through the cross connection 40 and pump system (not shown). For example, to perform an isocratic separation using solvent A, the valve 36A is actuated and maintained in an open state so that solvent A is drawn from the reservoir 38A and through the cross connection 40 and pump system while the other valves 36B, 36C and 36D are maintained in a closed state.

As described above for reverse purge embodiments, the static volumes of solvents in the portions of the fluid paths 86B, 86C and 86D between the valves 36B, 36C and 36D, respectively, and the corresponding valves 36B, 36C and 36D, respectively, can migrate over time into the fluid channel 78 leading from the cross connection 40 to the pump system. To perform an isocratic separation using solvent A and avoid the adverse consequences of solvent migration, a forward purge embodiment of a method for purging a fluid channel in a low pressure gradient formation liquid flow system can be used to replace the static volumes of solvents B, C and D with solvent A. Consequently, any subsequent migration of a static volume of solvent A into the fluid channel 78 downstream from the cross connection 40, which already contains solvent A, will not adversely affect the isocratic separation.

Figure 10B:
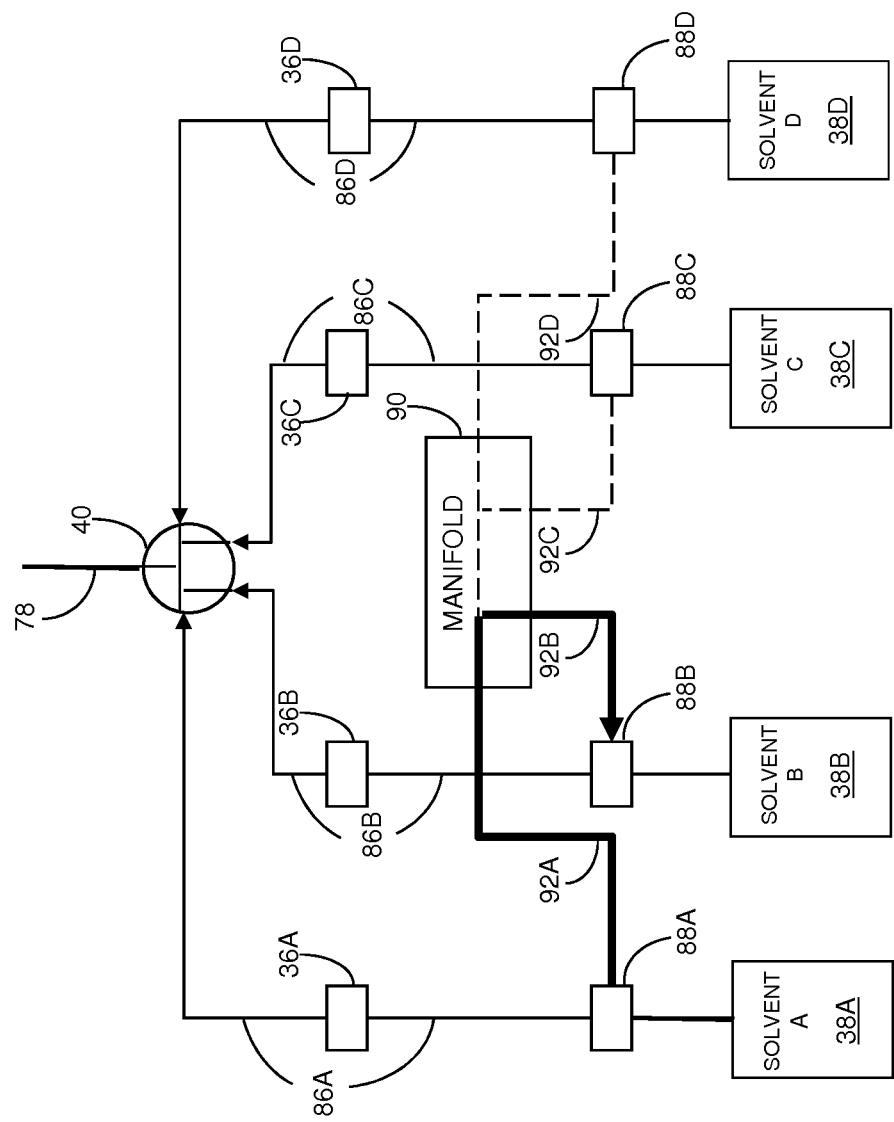
Figure 10C:
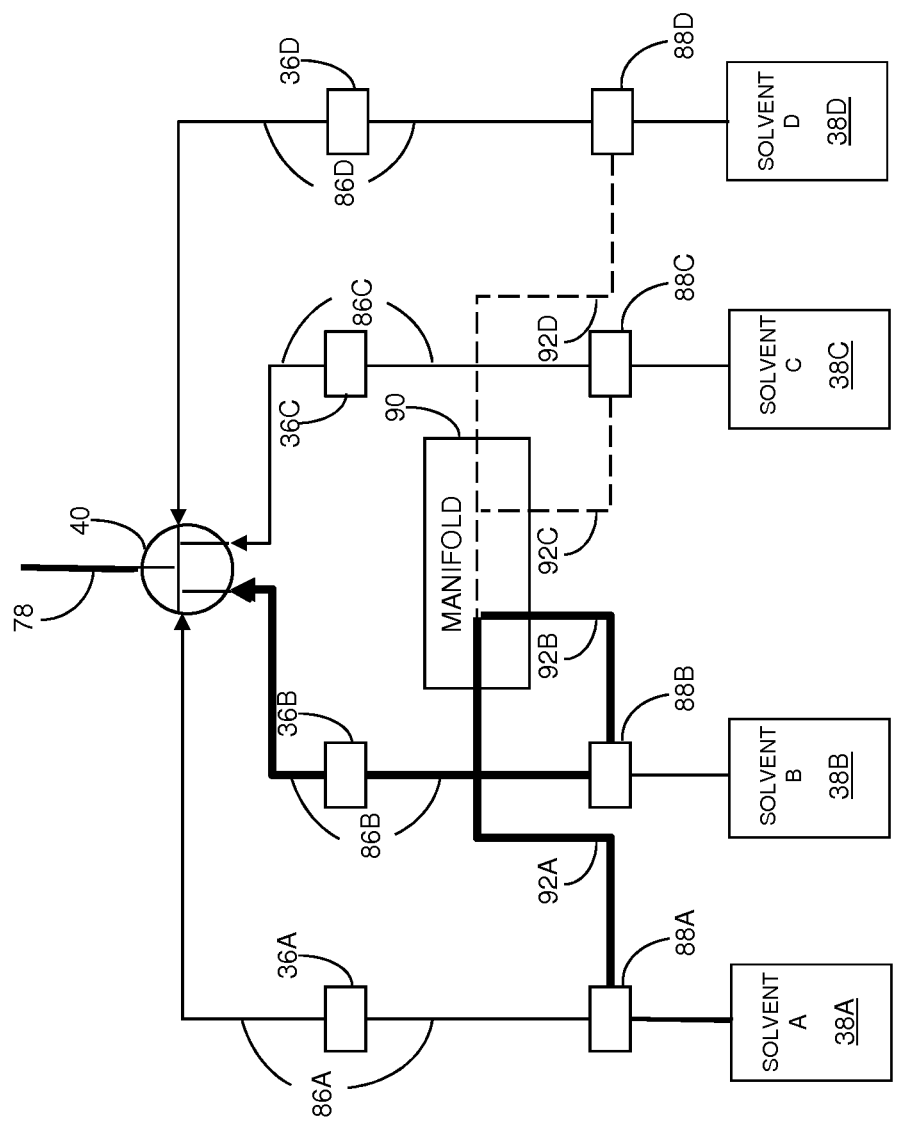
Figure 10D:
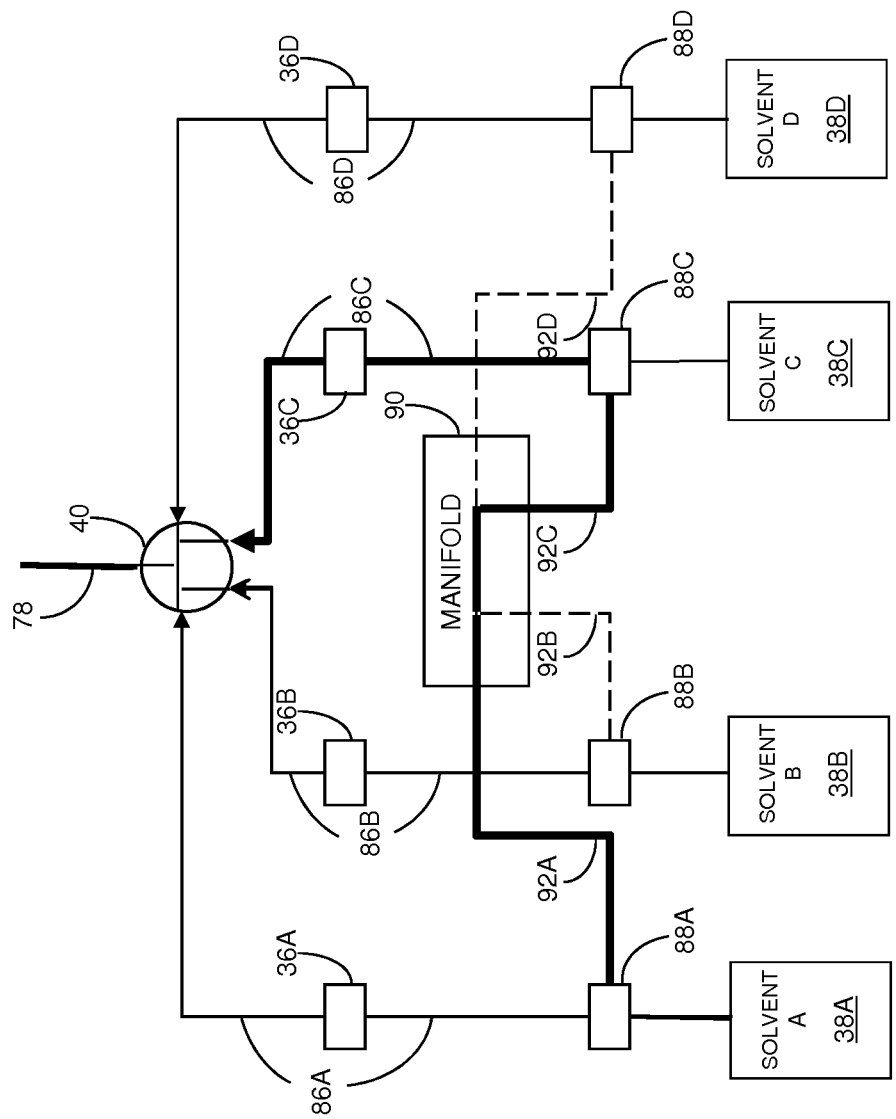
Figure 10E:
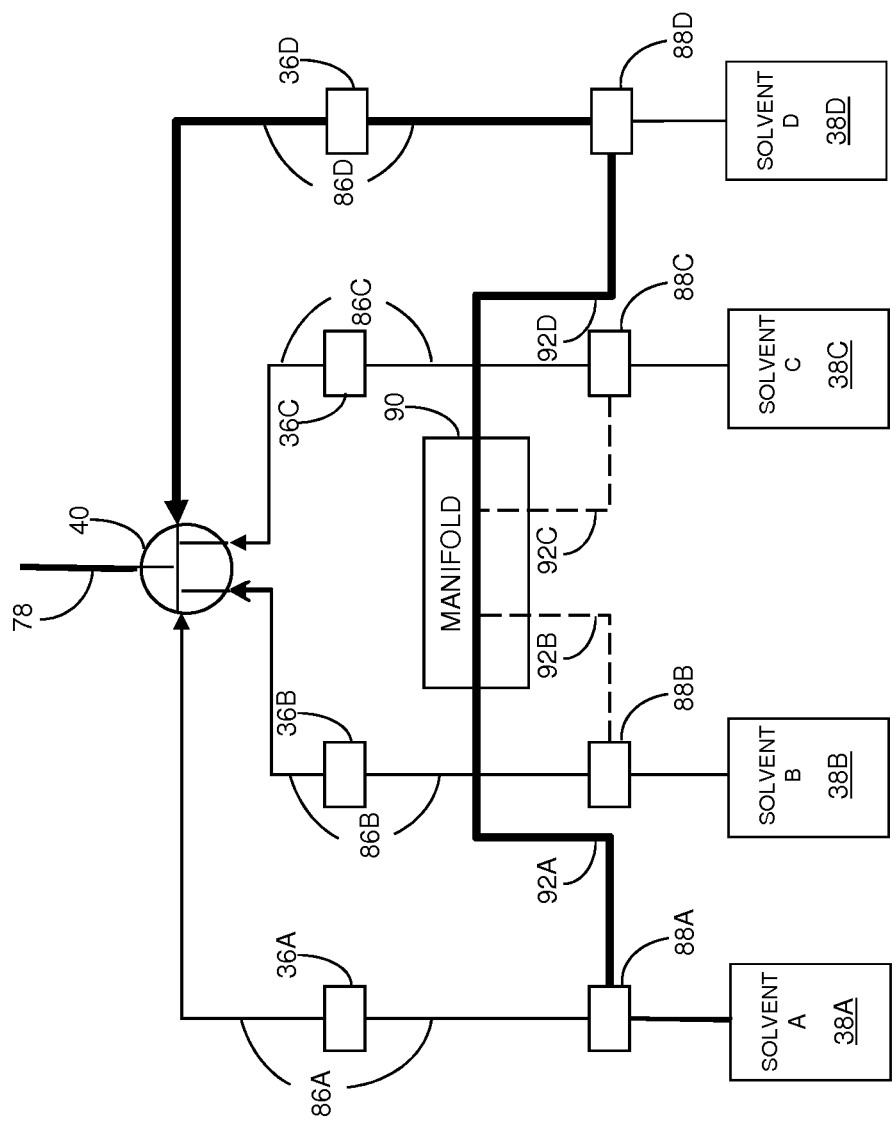
Figure 11:
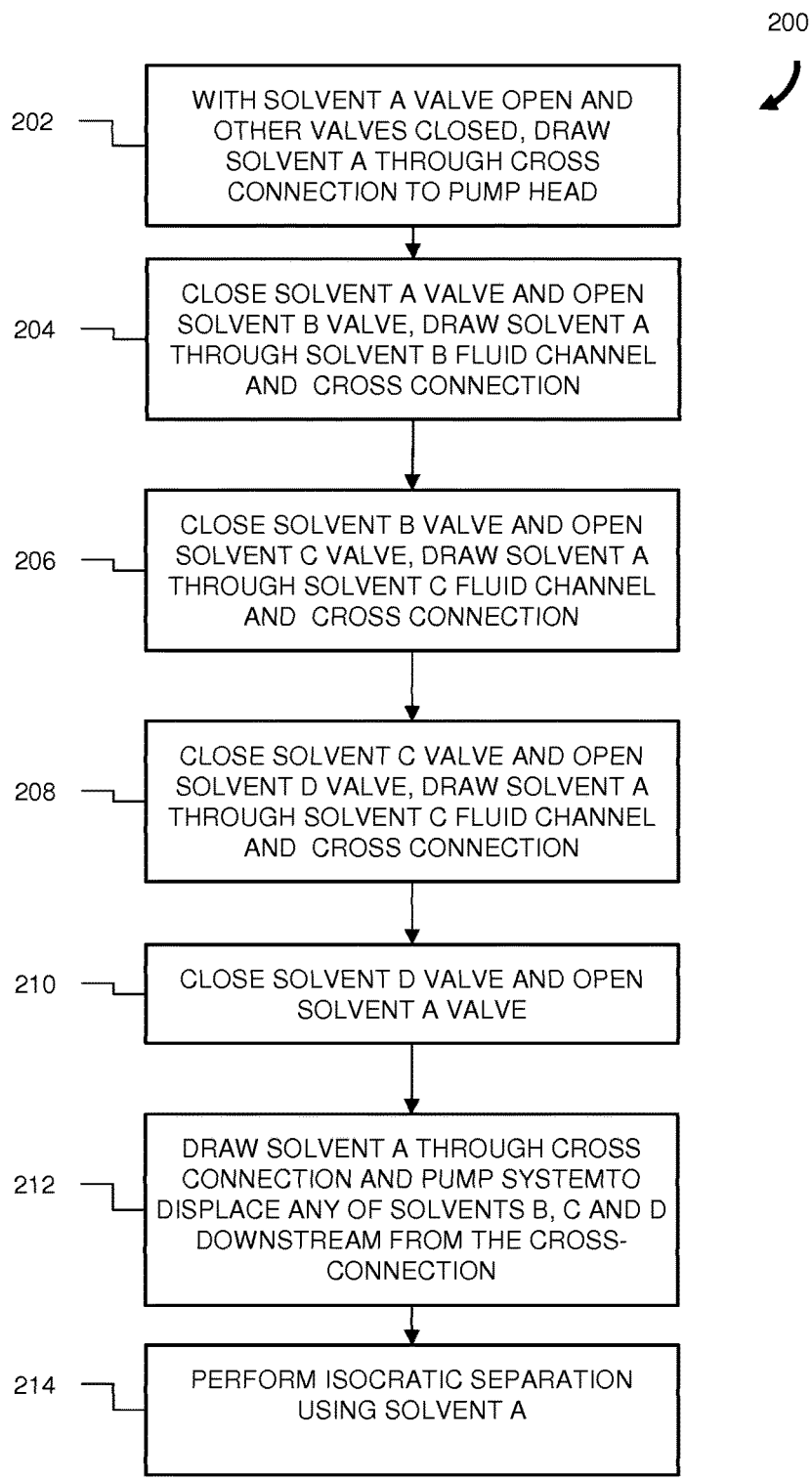
FIG. 11 is a flowchart of an embodiment of a method for forward purging a fluid channel in a low pressure gradient formation liquid flow system.

Reference is made here to the various views shown in FIG. 10A to FIG. 10E in conjunction with reference to the flowchart of an embodiment of the method 200 as shown in FIG. 11. Initially, all the solvent valves 36 are closed except for the valve 36A for solvent A. Solvent A is drawn (202) into fluid channels 86A and 78, and through to the pump system as shown in FIG. 10A. The valve 36A for solvent A is then closed, the solvent A and B two-position divert valves 88A and 88B are both changed to be in the second (divert) state and valve 36B is opened. This reconfiguration of valves allows solvent A to be drawn (204) through fluid channel 92A, the manifold 90, and fluid channel 92B as shown in FIG. 10B. The fluid continues by passing into fluid channel 86B to displace the static volume of solvent B as shown in FIG. 10C. The method 200 continues by reconfiguring the states of valves 36 and two-position divert valves 88 to perform steps 206 and 208 so that the volume of solvent C is displaced from fluid channel 86C as depicted in FIG. 10D. The states of the valves 36 and two-position divert valves 88 are reconfigured again to perform steps 210 and 212 so that the static volume of solvent D is displaced from fluid channel 86D as shown in FIG. 10E. The amount of solvent A used to displace the static volumes of solvents B, C and D can vary. Preferably, a sufficient volume of solvent A is drawn through the pump system after completing step 212 so that the displaced volumes of solvents B, C and D are directed to a waste port in the liquid chromatography system before commencing the isocratic separation in step 214.

While the invention has been shown and described with reference to specific embodiments, it should be understood by those skilled in the art that various changes in form and detail may be made therein without departing from the spirit and scope of the invention as recited in the accompanying claims. For example, although the embodiments described above are primarily directed to liquid chromatography applications, it should be recognized that the method is suitable for other liquid flow systems having similar liquid routing configurations for which displacement of various static volumes of liquid are desired. In addition, various embodiments above are directed to systems employing four different solvents or liquids; however, it should be realized that embodiments of the method can be used to purge one or more fluid channels in any system configured for use with two or more different liquids.

What is claimed is:

1. A method for purging a fluid channel in a low pressure gradient formation liquid flow system, the method comprising:

in a flow system having a cross connection, a first valve in communication with the cross connection through a first fluid channel, a second valve in communication with the cross connection through a second fluid channel, and a pump system in communication with the cross connection through a third fluid channel, the first fluid channel having a volume containing a first liquid and the second fluid channel having a volume containing a second liquid, drawing the first liquid from the first valve through the first fluid channel, the cross connection, the third fluid channel, and the pump system;

closing the first valve to prevent flow between the cross connection and the first valve;

opening the second valve to permit flow between the cross connection and the second valve;

supplying the first liquid from the pump system through the third fluid channel, the cross connection, and the second fluid channel to at least the second valve to thereby replace the volume of the second liquid in the second fluid channel with the first liquid; and closing the second valve to thereby prevent flow between the second valve and the cross connection.

2. The method of claim 1 wherein a volume of the first liquid that is supplied past the cross connection to at least the second valve is greater than the volume of the second fluid channel.

3. The method of claim 1 wherein the first and second valves are integral to a gradient proportioning valve.

4. The method of claim 1 further comprising opening the first valve and drawing the first liquid from the first valve through the first fluid channel to the cross connection, from the cross connection through the third fluid channel to the pump system, and through the pump system.

5. A method for purging a fluid channel in a low pressure gradient formation liquid flow system, the method comprising:

in a flow system having a cross connection, a first valve in communication with the cross connection through a first fluid channel, a second valve in communication with the cross connection through a second fluid channel, and a pump system in communication with the cross connection through a third fluid channel, the first fluid channel having a volume containing a first liquid and the second fluid channel having a volume containing a second liquid, controlling the second valve to prevent the flow of liquid in the second fluid channel;

drawing the first liquid through the first fluid channel to the pump system so that the first liquid occupies the first channel and the third channel;

controlling the first valve to prevent the flow of liquid in the first fluid channel and controlling the second valve to enable the flow of liquid in the second channel; and controlling the pump system to push the first liquid in the third channel into the second channel to substantially replace the second liquid in the second channel with the first liquid.

* * * * *